US008543414B2

(12) United States Patent
Iwano et al.

(10) Patent No.: US 8,543,414 B2
(45) Date of Patent: Sep. 24, 2013

(54) MEDICAL QUESTION CONTENTS AUTOMATIC SELECTION SYSTEM

(75) Inventors: Kenji Iwano, Kanagawa (JP); Katsuyuki Kaneko, Kanagawa (JP); Shiro Honma, Kanagawa (JP)

(73) Assignee: Panasonic Corporation, Osaka (JP)

( * ) Notice: Subject to any disclaimer, the term of this patent is extended or adjusted under 35 U.S.C. 154(b) by 912 days.

(21) Appl. No.: 12/301,815

(22) PCT Filed: May 24, 2007

(86) PCT No.: PCT/JP2007/060573
§ 371 (c)(1),
(2), (4) Date: Nov. 21, 2008

(87) PCT Pub. No.: WO2007/136108
PCT Pub. Date: Nov. 29, 2007

(65) Prior Publication Data
US 2010/0234691 A1    Sep. 16, 2010

(30) Foreign Application Priority Data
May 24, 2006  (JP) ................................ 2006-143679

(51) Int. Cl.
*G06Q 50/00* (2012.01)
(52) U.S. Cl.
USPC .................................................. 705/2; 705/3
(58) Field of Classification Search
USPC ......................................................... 705/2, 3
See application file for complete search history.

(56) References Cited

U.S. PATENT DOCUMENTS

| 6,171,112 B1* | 1/2001 | Clark et al. | 434/322 |
| 2003/0216671 A1* | 11/2003 | Saruwarati et al. | 600/595 |
| 2005/0143630 A1* | 6/2005 | Darby et al. | 600/300 |
| 2006/0135859 A1* | 6/2006 | Iliff | 600/300 |

FOREIGN PATENT DOCUMENTS

| JP | 10-143578 A | 5/1998 |
| JP | 2000-148889 A | 5/2000 |
| JP | 2003-228278 A | 8/2003 |
| JP | 2005-316661 A | 11/2005 |

OTHER PUBLICATIONS

English language Abstract of JP 10-143578 A.
English language Abstract of JP 2000-148889 A.
Kawaguchi, "Web de Kenko Kanri," Nikkei PC21, Japan, Nikkei Business Publications, Inc., Jan. 1, 2001, vol. 6, No. 1, pp. 220-223.

* cited by examiner

*Primary Examiner* — Neha Patel
(74) *Attorney, Agent, or Firm* — Greenblum & Bernstein, P.L.C.

(57) ABSTRACT

A medical question contents automatic selection system for automatically selecting medical questions allocated to a patient from the medical questionnaire made by a medical professional. The medical question contents automatic selection system compares the correct answer rate threshold of the medical questions preset by the medical professional with the correct answer rate of the questions to the patient so as to estimate the educational level of the patient about health, compares the vital sign measurement value threshold preset by the medical professional with the vital sign measurement value of the patient so as to estimate the condition level of the patient, and automatically selects medical questions allocated to the patient depending on the educational level and the condition level of the patient. The medical question contents automatic selection system can allocate medical questions to the patient depending on the educational level of the patient about health and disorder condition level of the patient without troubling the medical professional.

11 Claims, 17 Drawing Sheets

MEDICAL QUESTION CONTENTS AUTOMATIC SELECTION SYSTEM

TECHNICAL FIELD

The present invention relates to an automatic question contents selection system for selecting questions to assign to a patient from a plurality of questions.

BACKGROUND ART

In the recent years, lifestyle diseases such as diabetes and heart diseases have been increasing due to the westernization of eating habits, the spread of automobiles and the arrival of the aging of the population. Reviewing lifestyles including eating habits, exercise, and good sleep, is the most effective way of improving such lifestyle diseases.

As a means for allowing lifestyle disease patients to learn about their diseases, Patent Document 1 discloses a system for providing questions to a patient automatically by a computer based on a medical knowledge base for question use built by the doctor. Further, this system is able to assess the conditions of a patient in a remote area from a result of answers to questions, and send the patient points of improvement in his/her lifestyle and advises.

However, the system in Patent Document 1 has a problem that the preinstalled medical knowledge base is enormous and that this medical knowledge base, built based on a doctor's subjective judgment, does not necessarily become the same if built by another doctor.

Further, Patent Document 2 discloses a system for selecting inquiries on a per respondent basis by a computer based on information stored in a holding means and transmitting question contents automatically.

FIG. 1 is a block diagram showing the configuration of the system disclosed in Patent Document 2. Respondent information holding means 12 of automatic question apparatus 10 stores information about the respondent. Question deciding means 14 decides inquiries on a per respondent basis based on the information stored in respondent information holding means 12. When a predetermined time arrives, dialogue means 16 connects communication line 30 to answering apparatus 20, which the respondent uses, transmits the question contents decided in question deciding means 14 and receives answers to the questions from answering apparatus 20. By this means, even when there is no one at the end of automatic question apparatus 10, it is possible to pre sent questions to individual respondents automatically and collect answers.

However, Patent Document 2 only discloses automatically providing questions based on the information about the respondent, and does not disclose upon what basis of judgement inquiries for the respondent are decided, and therefore the system of Patent Document 2 has a problem with feasibility.

Patent Document 1: Japanese Patent Application Laid-Open No. HEI 10-143578
Patent Document 2: Japanese Patent Application Laid-Open No. 2000-148889

DISCLOSURE OF INVENTION

Problems to be Solved by the Invention

As described above, with conventional systems for allowing patients to learn about lifestyle diseases and so on, there are problems that the building of the medical knowledge base and evaluation of question results are likely to reflect the doctor's subjective judgment, and that, depending on the details of evaluation, the system, which is a computer, represents the doctor and performs the diagnosis.

It is therefore an object of the present invention to provide a system that can determine objectively how much a patient knows about health including lifestyle improvement, and that, depending on how much knowledge the patient has, assign the patient questions adequate for the patient.

Means for Solving the Problem

The automatic question contents selection system of the preset invention includes: an input section that receives as input: a question group having at least one question including an inquiry for testing knowledge about health and a plurality of answer options to the inquiry; an answer by a respondent to the question of the question group; a right answer setting for setting whether or not each of the options is a right answer; a right answer rate (RAR) threshold for the question group; a vital sign measurement value of the respondent; and a vital sign measurement value threshold; a storage section that stores: the question group; the right answer setting; the right answer rate threshold; and the vital sign measurement value threshold; a control section that selects the question group to assign to the respondent, based on: a right answer rate comparison result obtained by comparing a right answer rate of answers by the respondent, calculated from answers by the respondent inputted from the input section and the right answer setting stored in the storage section, and the right answer rate threshold for the question group which the respondent answers; and a vital sign measurement value comparison result obtained by comparing the measurement value of the respondent received as input in the input section and the measurement value threshold stored in the storage section; and a display section that displays: the inquiry and the options of the question of the question group which the control section assigns to the respondent; and the right answer rate comparison result and the measurement value comparison result.

Advantageous Effect of the Invention

According to the present invention, it is possible to assign questions to a patient according to his/her education level about health and symptom level of diseases, without troubling medical professionals. Further, the present invention makes it possible to objectively judge a patient's education level about health and symptom level of diseases, so that it is possible to provide to the patient information matching his/her education level about health and symptom level of diseases (by, for example, giving advices and telephone calls and showing educational videos).

BEST MODE FOR CARRYING OUT THE INVENTION

Now, embodiments of the present invention will be described in detail with reference to the accompanying drawings.

Embodiment 1

In Embodiment 1, an automatic question contents selection system for automatically selecting questions adequate for a patient without troubling medical professionals, based on the patient's right answer rate of answers to the inquiries of the questions prepared in advance by medical professionals including doctors and nurses, and presenting the questions to the patient, will be described. Here, a "question" means a pair of an inquiry asking whether the patient has knowledge about health (e.g. knowledge about diseases including lifestyle diseases) and a plurality of answer options to the inquiry. Further, a "question group" means a collected body of one or more questions. Part of a plurality of questions included in a question group may be messages without answers.

Figure 1:
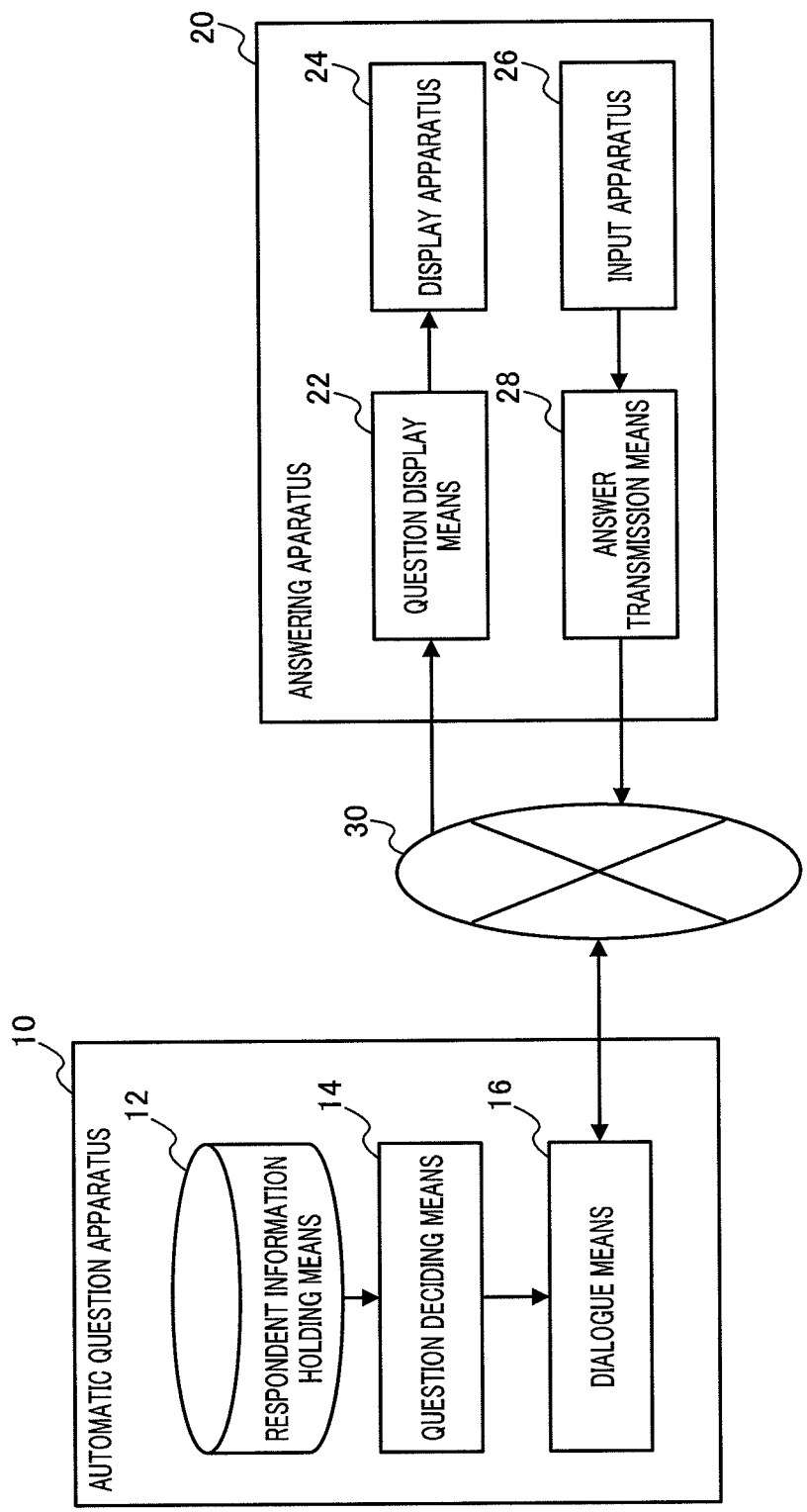
FIG. 1 is a block diagram showing the configuration of the conventional automatic dialogue system.
Figure 2:
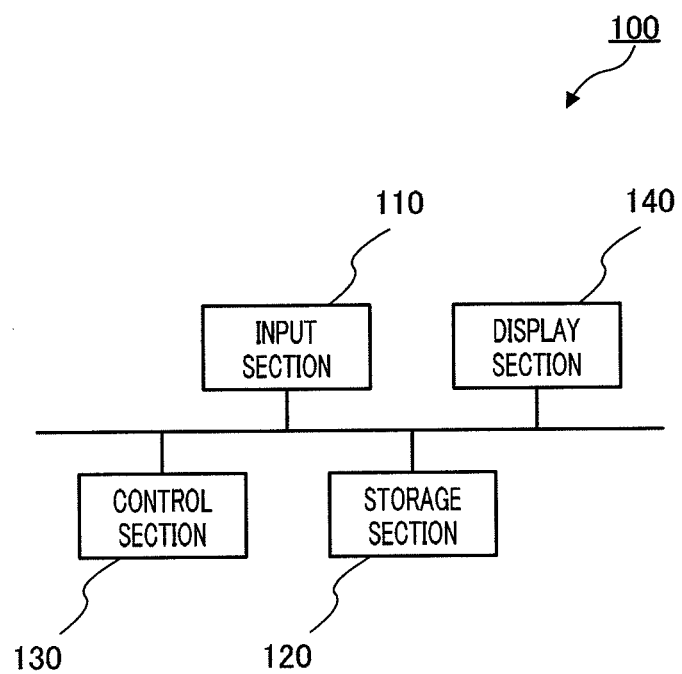
FIG. 2 is a block diagram showing the configuration of the automatic question contents selection system according to Embodiment 1 of the present invention.

FIG. 2 is a block diagram showing the configuration of the automatic question contents selection system according to Embodiment 1 of the present invention.

In FIG. 2, automatic question contents selection system 100 has input section 110, storage section 120, control section 130 and display section 140.

Input section 110 is an input means for doing inputs by medical professionals and by the patient. Input section 110 is, for example, a keyboard, mouse, jog dial, touch screen and so on, and is not particularly limited to these as long as medical professionals and the patient are able to operate inputs. As described later, from input section 110, medical professionals input: question groups including one or two or more questions; right answer setting for setting whether an answer option of the question is right; a right answer rate threshold each set for the question group; vital sign measurement value thresholds used upon determining the patient's symptom level and so on. On the other hand, the patient inputs answers to the questions in the question group assigned to the patient and his/her vital sign measurement values, through input section 110.

Storage section 120 stores the information inputted from input section 110 by medical professionals and the patient. For example, storage section 120 stores information including the question group, right answer setting, right answer rate threshold, vital sign measurement value threshold, the patient's answers, the patient's vital sign measurement values and so on, inputted from input section 110.

Control section 130 executes the process of preparing questions, process of providing settings to the questions, and process of selecting the question group to assign to the patient and so on. As explained later, control section 130 assesses the patient's education level about health from the patient's answers to the question and the right answer rate threshold stored in storage section 120, and selects a question group adequate for the patient based on the patient's education level (answer evaluation process). Further, control section 130 assesses the patient's symptom level from the his/her vital sign measurement values inputted from input section 110 and the vital sign measurement value threshold stored in storage section 120, and selects a question group adequate for the patient based on the patient's symptom level (measurement value evaluation process).

Display section 140 is an output means such as a display for allowing medical professionals or the patient to check the inquiries of the questions and the answer options and so on. For example, display section 140 displays the inquiries of the questions and answer options for the patient, and displays the result of the answer evaluation process and the result of the measurement value evaluation process for medical professionals.

In the configuration of FIG. 2, the contents in storage section 120 may be referred to from outside via communication lines (not shown). Further, the vital sign measurement values may be received as input from external systems via a communication section (not shown).

Here, the questions and question groups according to the present invention will be explained.

As mentioned earlier, a "question" according to the present invention refers to a pair of an inquiry asking whether the patient knows about health and a plurality of answer options to the inquiry. An example would be a pair of the inquiry "Is exercise good for preventing diabetes?" and two answer options "Yes" and "No."

Questions are classified into several types depending on in what manner the questions are answered. That is, the types of questions include: "single-selection question," in which the respondent chooses one answer option as an answer from a plurality of answer options to a question; "multiple-selection question" in which the respondent chooses one or two or more answer options as answers from a plurality of answer options to a question; "numeric value or text input question" in which the respondent inputs numbers or text as an answer to a question; and "question without answer," which simply notifies messages and does not require the respondent to input answers.

Figure 3:
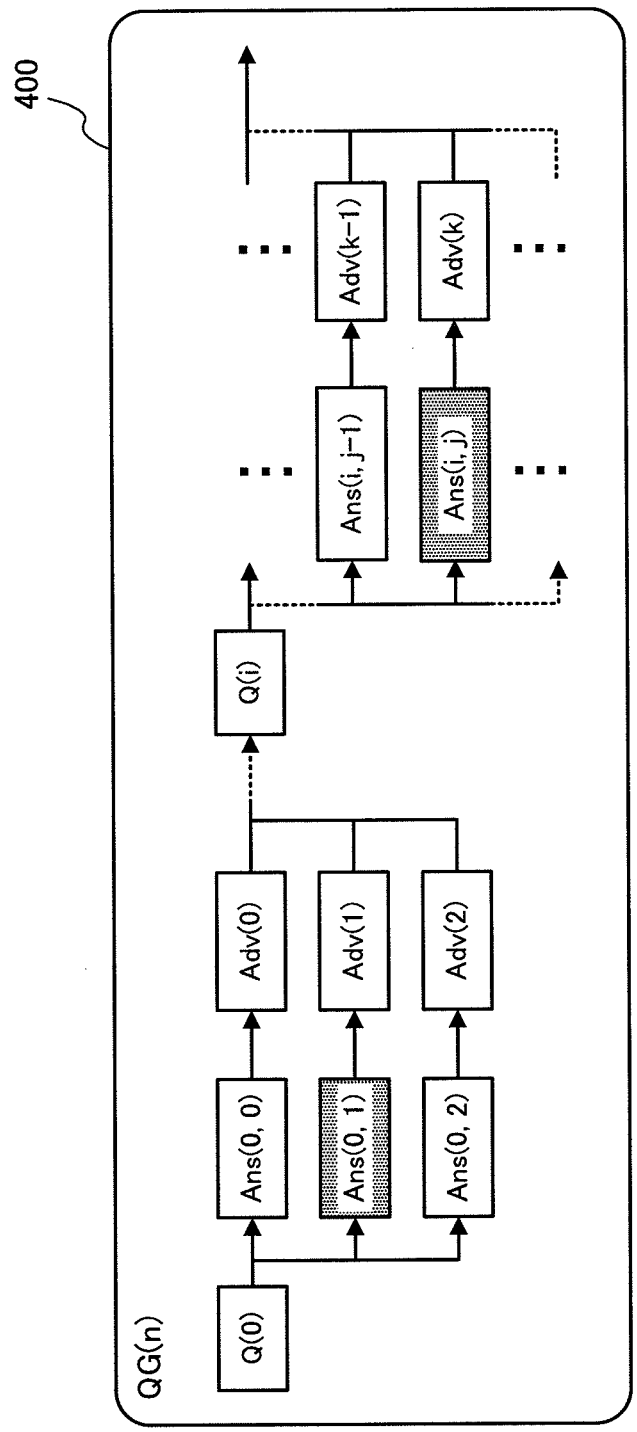
FIG. 3 illustrates the relationships between questions and question groups.

FIG. 3 illustrates the relationships between questions and question groups. Although a case will be described here single-selection questions are employed, multiple-selection questions apply likewise, except that a plurality of right answers can be set up in the question.

In one or two or more question groups stored in storage section 120, the n-th question group is represented as QG(n). In FIG. 3, question group QG(n) 400 consists of I questions.

Here, given that there are J answer options to the inquiry Q(i) of the i-th question, the j-th answer option is represented as an (i, j) ($0 \leq i < I$, $0 \leq j < J$). Although in FIG. 3 the right answer options are shown with gray squares, the right answer option (e.g. Ans(i, j)) is set up like "Ans(i, j)=1" and a wrong answer option (e.g. Ans(i, j−1)) is set up like "Ans(i, j−1)=0."

Further, when the patient chooses an answer option Ans(i, j) and an advice matching the answer is displayed, as shown in FIG. 3, after the patient chooses the answer option, the applicable k-th advice Adv(k) may be displayed. In this way, one question is generally composed of an inquiry Q(i), answer options Ans(i, j) and advices Adv (k), but in some cases there may be no advice Adv (k). Although a setup is presented with the example shown in FIG. 3 where the respondent moves onto next inquiry of the questions in order regardless of which answer options the respondent chooses, a setup is equally possible where the next proceeding question changes depending on which answer options are chosen.

Figure 4:
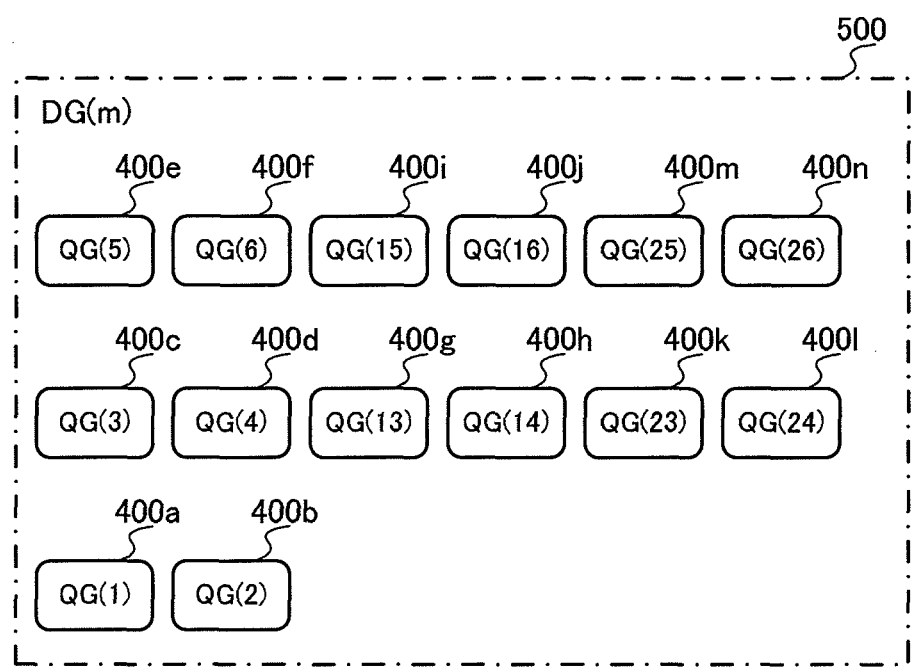
FIG. 4 illustrates the relationships between question groups and disease groups.

FIG. 4 illustrates the relationships between question groups and disease groups. The "disease groups" refer to groups including one or two or more question groups classified by diseases such as diabetes, heart failure and asthma. Here, the m-th disease group in a plurality of disease groups is represented as DG(m). Disease group DG(m) is consist of one or two or more question groups QG(n) having questions related to the disease. In the example shown in FIG. 4, disease group DG(m) 500 is consist of fourteen question groups QG(n) 400a to 400n.

Figure 5:
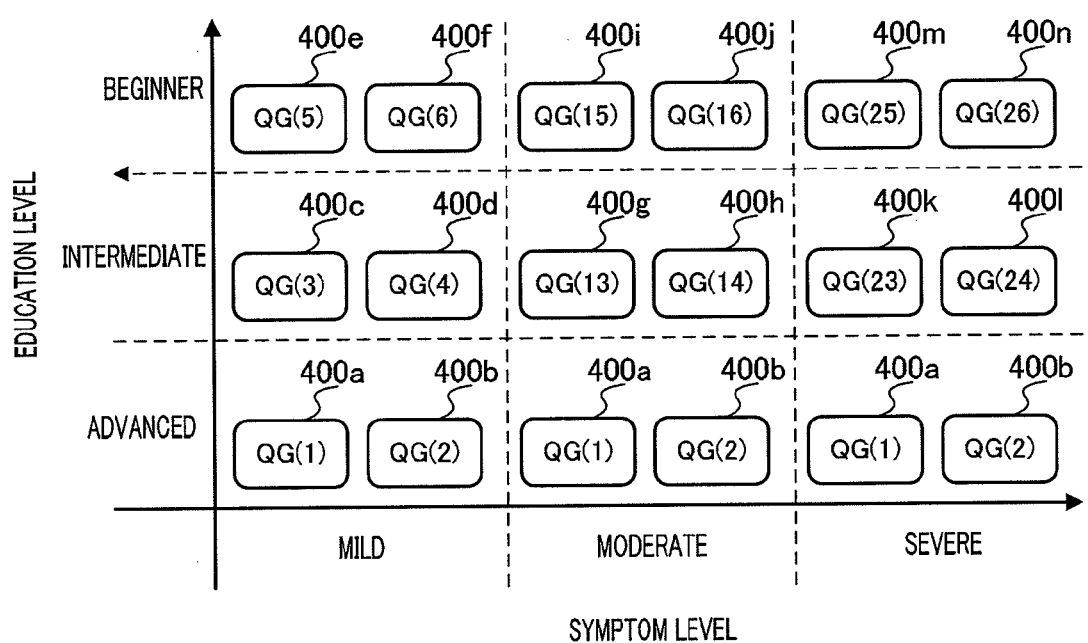
FIG. 5 illustrates the relationships between education levels and symptom levels.

FIG. 5 shows the situation where the question groups included in the disease group shown in FIG. 4 are classified by education levels and symptom levels. Although the disease group will be explained here as a disease group of diabetes for ease of description, other diseases are equally applicable.

First, question groups QG(1) 400a to QG(26) 400n, including questions for testing knowledge about diabetes, are classified according to the patient's education level subject to assignment. In FIG. 5, this is the classification in the vertical axis direction. For example, amongst diabetes patients, there are patients who understand less what kind of disease diabetes is and there are patients who are familiar with diet therapy, exercise therapy and so on. As described later, by classifying question groups according to the patient's education level, it becomes possible to assign the patient a question group that matches the patient's education level.

Here, a case will be explained as an example where education levels are classified into "beginner," "intermediate" and "advanced." Accordingly, a patient of the "beginner's" education level is presented a question in which the patient selects a single answer of "Yes" or "No" to the inquiry such as "Is exercise good for preventing diabetes?" The right answer to this inquiry is "Yes." Further, a patient of the "intermediate" education level is presented a question in which the patient selects a single answer of "Yes" or "No" to the inquiry such as "To decrease the blood sugar level, would it be good to exercise hard (i.e. tough exercise) for a short period time?" The right answer to this inquiry is "No." To explain the right answer in more detail, it is generally settled that aerobics is more effective than anaerobics to lower the blood sugar level. Further, a patient of the "advanced" education level is presented a question in the patient selects a single answer of "Yes" or "No" to the inquiry such as "When a diabetes patient exercises walking, would it be good wearing white socks?" The right answer to this inquiry is "Yes." To explain the right answer in more detail, diabetes, if advanced, may develop into neuropathy and cause numbness in the legs, so that, by wearing white socks, the patient is able to notice when he/she bleeds.

Further, question groups QG(1) 400a to QG(26) 400n, including questions for testing knowledge about diabetes, are classified according to the symptom level of the patient subject to assignment. In FIG. 5, this is the classification in the horizontal axis direction. For example, amongst diabetes patients, there are "mild" patients who are able to cope with their disease only by diet therapy, exercise therapy and so on. Likewise, there are "moderate" patients who require medication therapy and there are "severe" patients who require insulin injections for their inadequate insulin secretion. Then, by classifying the question groups according to the patient's symptom levels, it becomes possible to assign the patient a question group that matches the patient's symptom level.

Here, a case will be explained as an example where symptom levels are classified into "mild," "moderate" and "severe." The "mild" symptom level covers patients who are able to cope with diabetes only by, for example, diet therapy or exercise therapy. The "moderate" symptom level covers patients having medication therapy, for example. The "severe" symptom level covers patients having insulin therapy, for example. Indicators for determining the symptom levels include vital sign measurement values such as the blood sugar level, whether or not the patient is medicated, and whether or not the patient is prescribed insulin. For example, when the blood sugar level (vital sign measurement value) is measured by a blood sugar monitor (vital sign monitor), the symptom level may be judged "mild" if the blood sugar level on an empty stomach is 126 mg/dl or lower and the blood sugar level two hours after meal is 200 mg/dl or lower. However, these thresholds for the blood sugar level are simply examples and are by no means limiting, for they should be set by medical professionals.

Although with the above example question groups are classified according to education levels and symptom levels into three levels each, the variations of levels set up for classifying question groups and the number of levels to be classified into are not limited to the above example.

The operations of automatic question contents selection system 100 configured as described above will be explained below. This automatic question contents selection system 100 presumes use of patients of lifestyle diseases and individual respondents who are interested in health (hereinafter collectively "patients") and medical professional such as doctors and nurses in medical institutions.

Figure 6A:
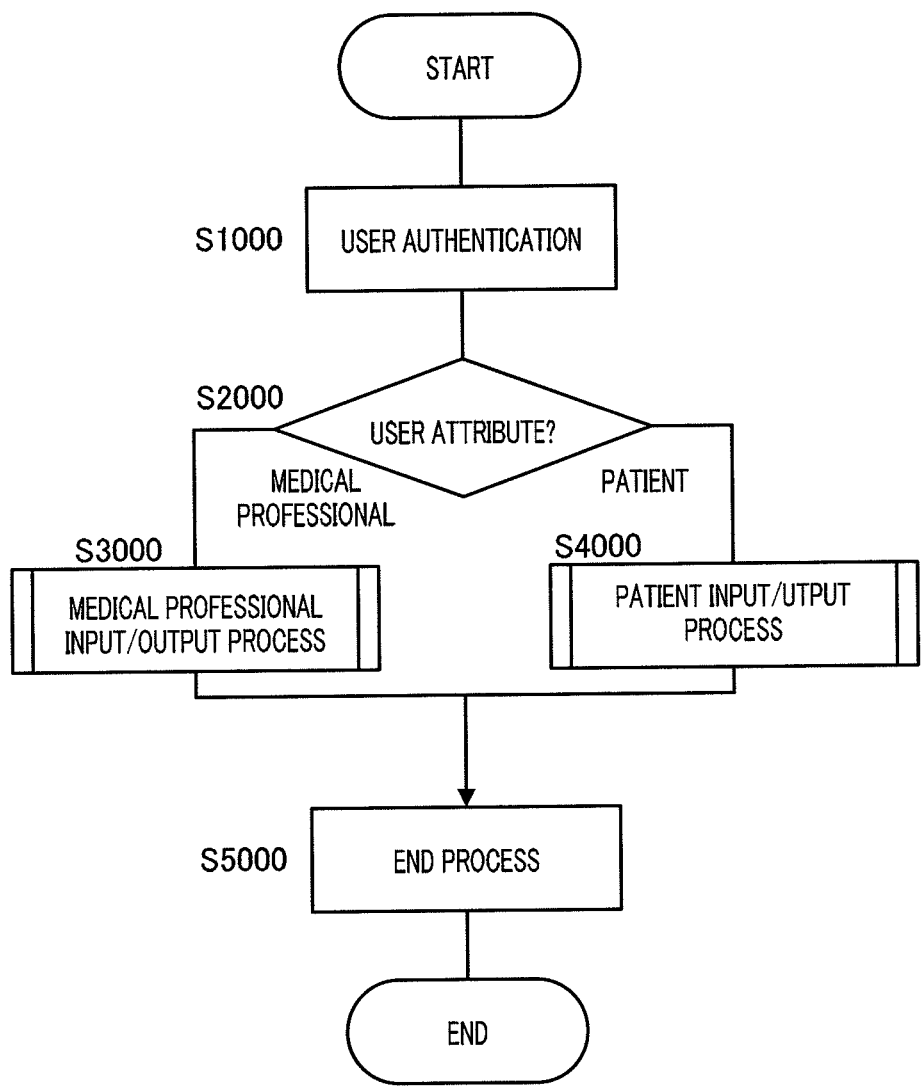
FIG. 6A is a flow chart showing the operations of the automatic question contents selection system according to Embodiment 1 of the present invention.

FIG. 6A is a flowchart showing the procedures of automatic question contents selection system 100.

First, in step S1000, control section 130 makes display section 140 display the user authentication screen to perform a user authentication process. Next, in step S2000, based on the result of the user authentication process, control section 130 decides whether the user attribute is a medical professional or a patient.

In step S2000, when control section 130 determines the user attribute is a medical professional (S2000: "medical professional"), the process moves to step S3000. In step S3000, medical professional performs medical professional input and/or output process including preparing questions, and the process moves to step S5000. Medical professional input/output process will be described later using FIG. 6B.

On the other hand, in step S2000, when control section 130 determines the user attribute is a patient (S2000: "patient"), the process moves to step S4000. In step S4000, the patient performs patient input and/or output process including answering the inquiries of the questions, and the process moves to step S5000. The patient input/output process will be described later using FIG. 6C.

In step S5000, control section 130 performs the end process including logging out the user from the system, to finish the process.

Next, medical professional input/output process in FIG. 6A (step S3000) will be explained using the flow chart shown in FIG. 6B.

First, in step S3100, control section 130 makes display section 140 display the process selection screen, to allow medical professional (user) choose the desired process. Here, a case will be described where display section 140 makes the user choose one of four processes, namely the "question setup process" of preparing the questions and providing various settings, the "assigning patient process" of performing initial settings for the question group assigned to the patient, the "answer evaluation result display process" of showing the result of the answer evaluation process (described later) of the patient's answers to the questions, and the "end process" of finishing medical professional input/output process.

Next, in step S3200, control section 130 determines the process medical professional chooses in step S3100. When medical professional chooses the question setup process (S3200: "question setup process"), the question setting process is performed in step S3300, and the process returns to step S3100. The question setup process will be described later using FIGS. 7A and 7B. When medical professional chooses the assigning patient process (S3200: "assigning patient process"), the assigning patient process is performed in step S3400, and the process returns to step S3100. The assigning patient process will be described later using FIG. 8. When medical professional chooses the answer evaluation result display process (S3200: "answer evaluation result display process"), in step S3500, control section 130 makes display section 140 display the result of the answer evaluation process (described later) of the patient's answers to the questions, and the process returns to step 53100. By checking the result of the answer evaluation process, medical professional can determine the patient's education level about health objectively.

On the other hand, in step S3200, when medical professional chooses the end process (S3200: "end process"), medical professional input/output process (step S3000) is finished, and the process moves to step S5000 in FIG. 6A.

Next, patient input/output process in FIG. 6A (step S4000) will be explained using the flow chart shown in FIG. 6C.

First, in step S4100, control section 130 makes display section 140 display the process selection screen, to allow the patient (user) to choose the desired process Here, a case will be described where display section 140 make the user choose one of three processes, namely the "question answering process" of answering the question assigned to the patient, the "vital sign measurement value input process" of inputting the patient's vital sign measurement values, and the "end process" of finishing the patient input/output process.

Next, in step S4200, control section 130 determines the process the patient chooses in step S4100.

When the patient chooses the question answering process (S4200: "question answering process"), the question answering process is performed in step S4300. The question answering process will be described later using FIG. 9. Next, in step S4400, the answer evaluation process of selecting the question group to assign to the patient based on the details of the patient's answers in the question answering process (step S4300), is performed, and the process returns to step S4100. The answer evaluation process will be described later using FIGS. 10A and 10B.

On the other hand, when the patient chooses the vital sign measurement value input process (S4200: "vital sign measurement value input process"), in step S4500, the patient inputs his/her vital sign measurement values measured with a vital sign monitor via, for example, input section 110. The kinds of the vital signs inputted then may be determined as appropriate depending on the patient's disease. For example, a diabetes patient may input his/her blood sugar level (i.e. vital sign measurement value) measured with a blood sugar level sensor (i.e. vital sign monitor) via input section 110 or a communication section (not shown). Next, in step S4600, the measurement value evaluation process of setting up the question group to assign to the patient based on the vital sign measurement values inputted by the patient in the vital sign measurement value input process (step S4500), is performed, and the process returns to step S4100. The measurement value evaluation process will be described later using FIG. 11.

On the other hand, in step S4200, when the patient chooses the end process (S4200: "end process"), the patient input/output process (step S4000) is finished, and the process moves to step S5000 in FIG. 6A.

As described above, if the user is a medical professional, automatic question contents selection system 100 performs, as medical professional input/output process, the question setup process (described later using FIGS. 7A and 7B), assigning patient process (described later using FIG. 8) or answer evaluation result display process, depending on what medical professional desires. On the other hand, if the user is a patient, automatic question contents selection system 100 performs, as the patient input/output process, the question answering process with the answer evaluation process (described later using FIGS. 9, 10A and 10B), or the vital sign measurement value input process with the measurement value evaluation process (described later using FIG. 11), depending on what the patient desires.

Next, the question setup process (step S3300) and assigning patient process (step S3400) performed in medical professional input/output process (step S3000) of FIG. 6B will be explained.

Question Setup Process

The question setup process (step S3300) of FIG. 6B will be explained using the flow chart shown in FIGS. 7A and 7B. FIG. 7A shows the first half of the flow chart and FIG. 7B shows the second half of the flow chart.

First, in step S3301, control section 130 makes display section 140 display the question setup screen. Next, in step S3302, control section 130 makes medical professional choose the question group to which a new question to be prepared belongs and set up the education level and symptom level of the question group.

Next, in step S3303, control section 130 makes display section 140 display the question type selection screen, to make medical professional choose the type of the new question. Here, as described above, it is explained that control section 130 makes medical professional choose one of a single-selection question, multiple-selection question, numeric value or text input question, and question without answers.

Next, in step S3304, control section 130 determines the type of the question chosen by medical professional in step S3303. When medical professional chooses a single-selection question (S3304: "single-selection question"), the process moves to step S3305 to prepare a single-selection question. When medical professional chooses a multiple-selection question (S3304: "multiple-selection question"), the process moves to step S3308 to prepare a multiple-selection question. When medical professional chooses a numeric value or text input question (S3304: "numeric value or text input question"), the process moves to step S3311 to prepare a numeric value or text input question. When medical professional chooses a question without answers (S3304: "question without answers"), the process moves to step S3313 to prepare a question without answers.

To prepare a single-selection question (S3304: "single-selection question"), in step S3305, control section 130 makes medical professional input an inquiry for the question and a plurality of answer options to the inquiry, via input section 110. Next, in step S3306, control section 130 asks the medical professional whether the answer options for the question prepared in step S3305 includes the right answer. For example, in the case of testing knowledge about health in quiz format, if a plurality of answer options include a single right answer, medical professional judges that the answer options for the question include the right answer. Furthermore, in the case of testing knowledge about lifestyles and living conditions where the concept of the right answer is inapplicable, in a plurality of answer options, medical professional judges that the answer options for the question include no right answer. When a plurality of answer options for the question include the right answer (S3306: "YES"), in step S3307, control section 130 makes medical professional choose the right answer option via input section 110. Control section 130 sets a right answer flag to the chosen answer option, and the process moves to step S3314. On the other hand, when there is no right answer in the answer options in the question (S3306: "NO"), the process moves directly to step S3314 without providing a right answer flag.

To prepare a multiple-selection question (S3304: "multiple-selection question"), in step S3308, control section 130 makes medical professional input inquiries for the question and a plurality of answer options for each question, via input section 110. At this time, control section 130 provides settings such that the patient is able to choose multiple answer options for one question. Next, in step S3309, control section 130 asks the medical professional whether the answer options for the question include the right answer, in step S3308. If the answer options for the question include the right answer (S3309: "YES"), in step S3310, control section 130 makes medical professional choose the right answer option via input section 110. At this time, control section 130 may make medical professional choose a plurality of right answer options. Control section 130 provides a right answer flag to the chosen answer options, and the process moves to step S3314. On the other hand, if the answer options for the question include no right answer (S3309: "NO"), the process moves directly to step S3314 without setting a right answer flag.

To prepare a numeric value or text input question (S3304: "numeric value or text input question"), in step S3311, control section 130 makes medical professional input the inquiries of the questions via input section 110. Next, in step S3312, if necessary, control section 130 makes medical professional input the upper limit value and lower limit value that can be received as answers via input section 110. Control section 130 sets up the values inputted then as the upper limit value and lower limit value that can be received as answers, and the process moves to step S3314.

To prepare a question without answers (S3304: "question without answers"), in step S3313, control section 130 makes medical professional input messages to notify to the patient, via input section 110, and the process moves to step S3314.

In step S3314, control section 130 asks the medical professional whether all the questions for the question group chosen in step S3302 have been prepared. If the preparations of the questions is not finished (S3314: "NO"), the process returns to step S3303 and a new question starts being prepared. Consequently, steps S3303 to S3314 repeat until all the questions of the question group chosen in step S3302 have been prepared. Meanwhile, if the preparation of all the questions is finished (S3314: "YES"), the process moves to step S3315.

In step S3315, control section 130 determines whether there is at least one question where the right answer flag is set, in the series of questions prepared in steps S3303 to S3313. If there are the questions where the right answer flag is set (S3315: "YES"), the process moves to step S3316. On the other hand, if there is no question where a right answer flag is set (S3315: "NO"), the process moves to step S3324.

In step S3316, with respect to the series of questions prepared in steps S3303 to S3313, control section 130 asks the medical professional whether to assign weight to the questions on a per question basis. If weight is assigned to the questions on a per question basis (S3316: "YES"), in step S3317, control section 130 makes medical professional input the question weight coefficient W(i) to assign to each question via input section 110. Control section 130 sets up the inputted question weight coefficients W(i) to the questions, and the process moves to step S3318. For example, medical professional assigns greater weight to questions of higher significance and assigns less weight to questions of lower significance. On the other hand, if weight is not assigned (S3316: "NO"), the process moves to S3318 without assigning weight to the questions. At this time, as a default setup of automatic question contents selection system 100, instead of not assigning weight, questions belonging to the same question group may be assigned equal weight.

In step S3318, with respect to the multiple-selection questions in the series of questions prepared in steps S3303 to S3313, control section 130 asks the medical professional whether to assign weight to the answer options on a per answer option basis. If weight is assigned to the answer options on a per answer option basis (S3318: "YES"), in step S3319, control section 130 makes medical professional input weight to assign to the individual answer options for all of the multiple-selection questions, via input section 110. Control section 130 sets up the inputted weight to the answer options of the questions, and the process moves to step S3320. Medical professional assigns, for example, greater weight to answer options of higher significance and assigns less weight to answer options of lower significance. This setup makes it possible to set right answer rates that medical professional thinks adequate. On the other hand, if weight is not assigned (S3318: "NO"), the process moves to S3320 without assigning weight to the answer options.

In step S3320, control section 130 asks the medical professional whether to refer to the history of earlier answers, in the answer evaluation process (described later, see FIGS. 10A and 10B), with respect to the question group chosen in step S3302. To refer to the history of answers (S3320: "YES"), in step S3321, control section 130 makes medical professional input the number of times of making reference to the history of answers, via input section 110. Control section 130 sets the number of times of making reference to the history of answers inputted then, with respect to the question group chosen in step S3302, and the process moves to step S3322. By calculating the right answer rate from a plurality of answers to one question, medical professional is able to determine whether the patient has chosen the right answer option by chance. If, on the other hand, reference is not made to the history of answers (S3320: "NO"), the process moves to step S3322 without setting up the number of times of making reference to the history of answers.

In step S3322, control section 130 makes medical professional input the right answer rate threshold for the question group chosen in step S3302 via input section 110. Here, the "right answer rate threshold" refers to a value that serves as the basis for deciding whether or not control section 130 switches the question group to assign to the patient in the answer evaluation process (described later with reference to FIGS. 10A and 10B) to a different, unanswered question group. For example, for a given question group, if the patient's right answer rate of answers to the questions is compared with the right answer rate threshold set for the question group and the patient's right answer rate proves equal to or higher than the right answer rate threshold, the question group to assign to the patient is switched to a different, unanswered question group.

Next, in step S3323, control section 130 asks the medical professional whether or not the setup of the right answer rate threshold for the question group chosen in step S3302 is finished. If the setup of the right answer rate threshold is not finished (S3323: "NO"), the process returns to step S3316. On the other hand, if the setup of the right answer rate threshold is finished (S3323: "YES"), control section 130 stores the contents set up in steps S3302 to S3322, where necessary, in storage section 120, and the process moves to step S3324.

Figure 6B:
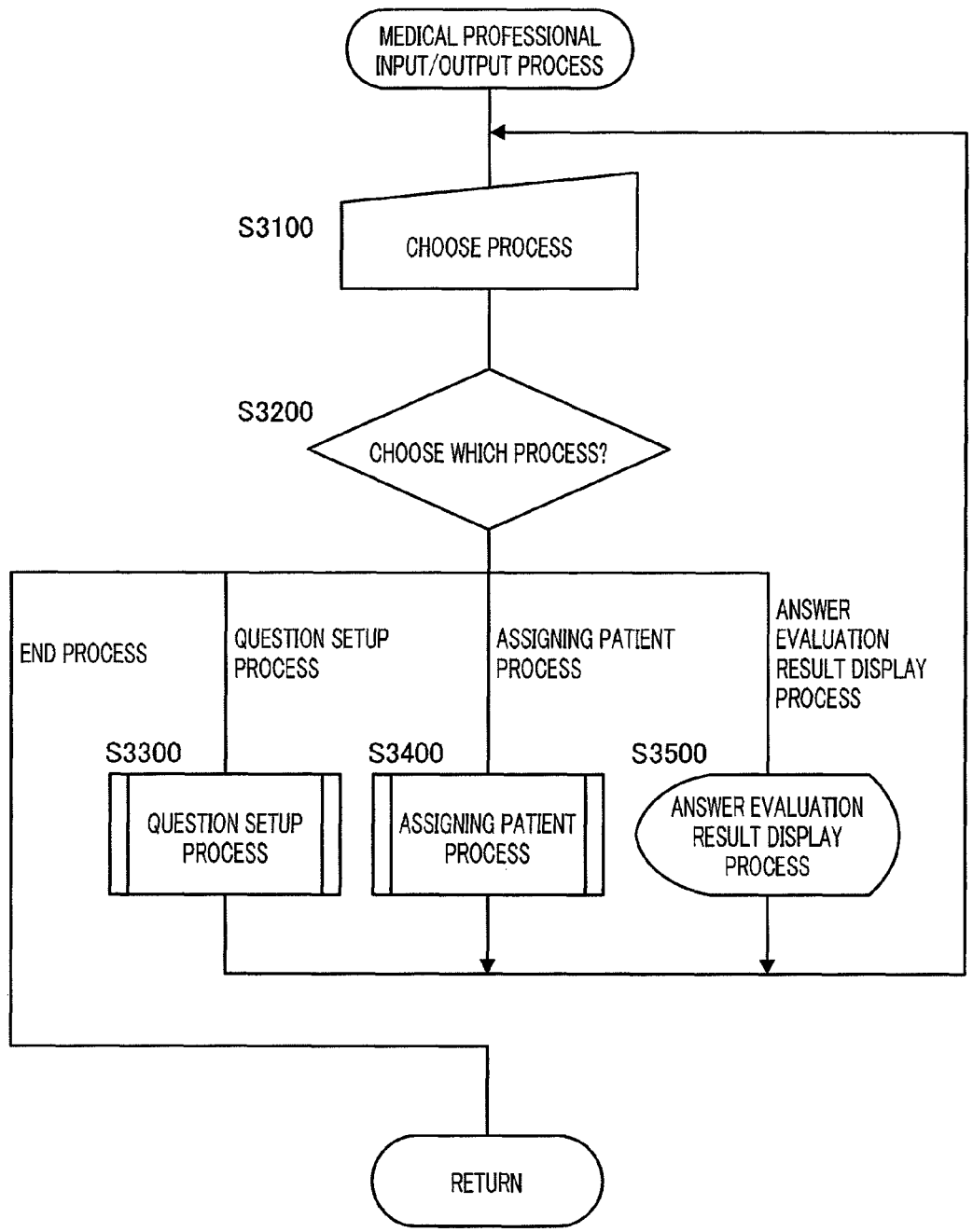
FIG. 6B is a flow chart showing the procedures of medical professional input/output process of FIG. 6A.
Figure 7A:
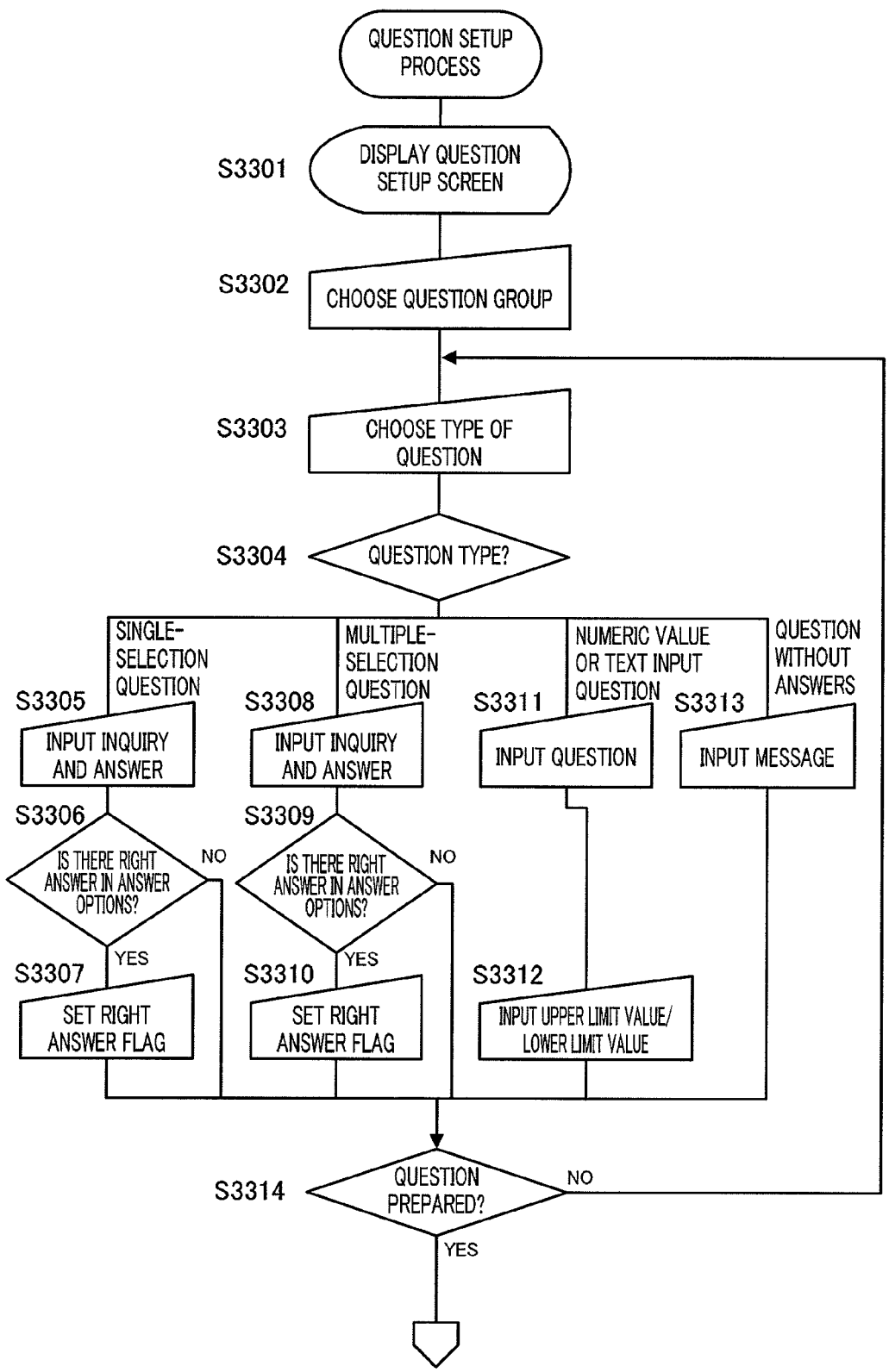
FIG. 7A is a flow chart showing the procedures of the question setup process (the first half) of FIG. 6B.
Figure 7B:
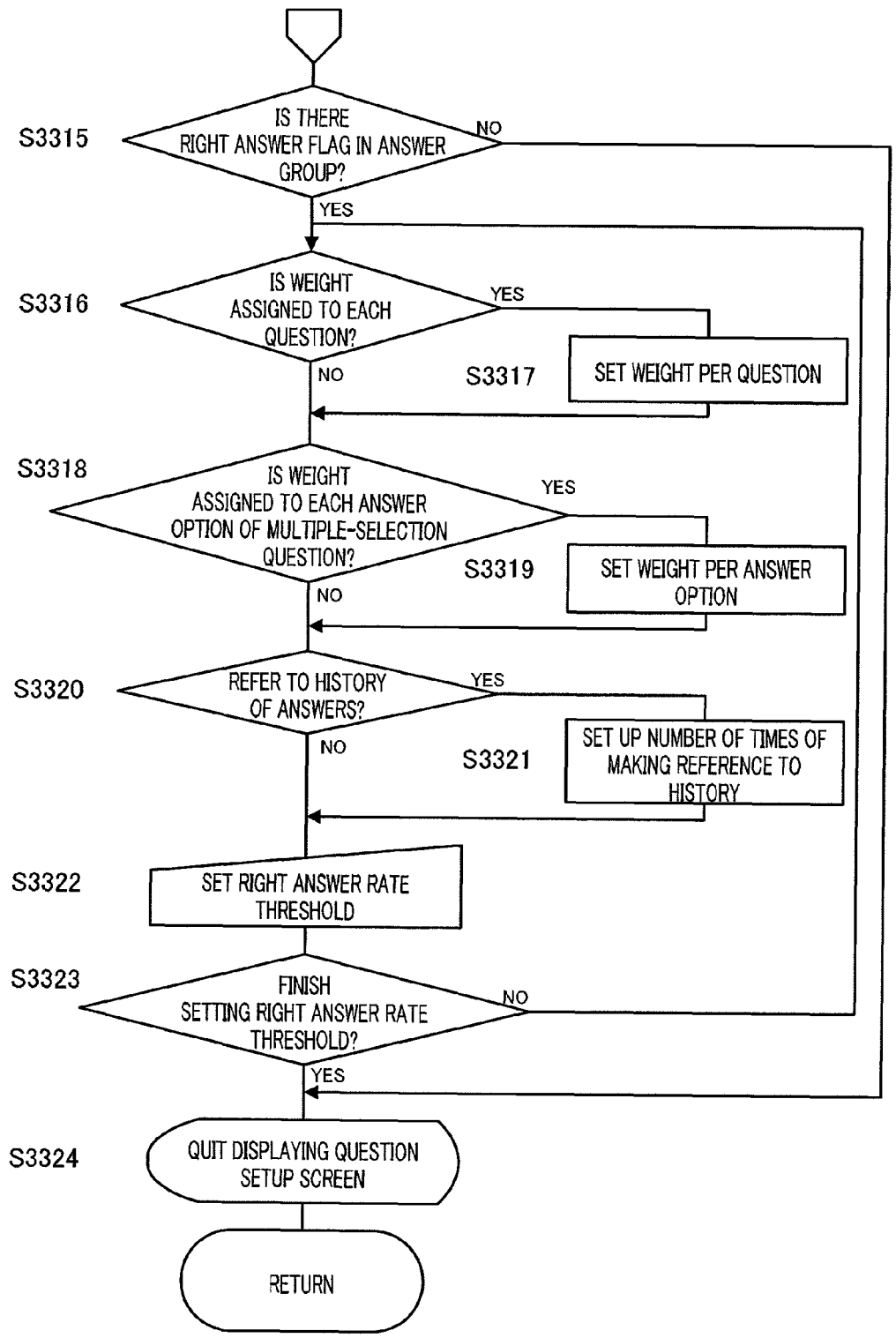
FIG. 7B is a flow chart showing the procedures of the question setup process (the second half) of FIG. 6B.

In step S3324, control section 130 makes display section 140 quit displaying the question setup screen, and, upon finishing the question setup process (step S3300), the process moves to step S3100 of FIG. 6B.

Assigning Patient Process

Figure 8:
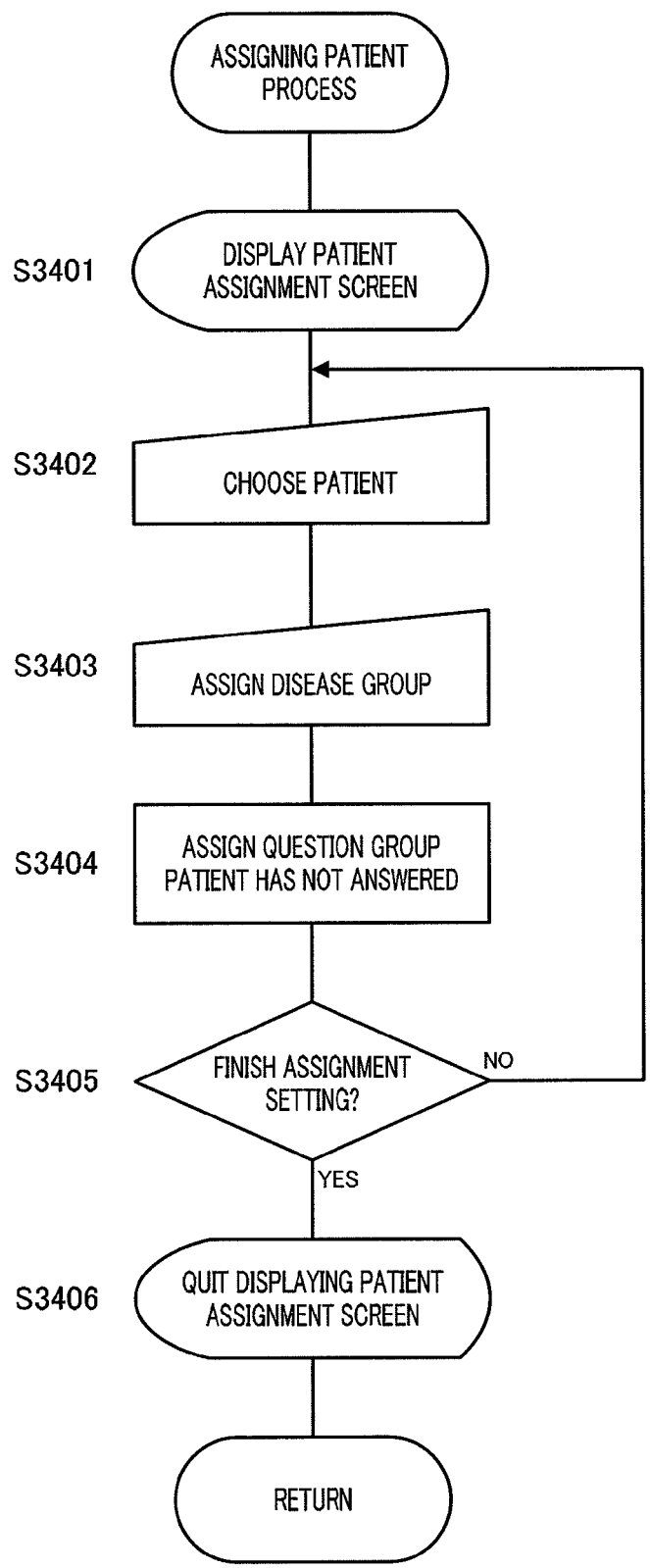
FIG. 8 is a flow chart showing the procedures of the assigning patient process of FIG. 6B.

Next, the assigning patient process (step S3400) of FIG. 6B will be explained using the flow chart shown in FIG. 8.

First, in step S3401, control section 130 makes display section 140 display the patient assignment screen.

Next, in step S3402, control section 130 asks the medical professional (user) about the patient subject to assignment the question group and makes medical professional choose the patient via input section 110.

Next, in step S3403, control section 130 asks the medical professional about the disease group to assign to the patient chosen in step S3402, and makes medical professional choose the disease group via input section 110. Next, in step S3403, control section 130 reads the education level and symptom level of the patient chosen in step S3402 from the setup information stored in storage section 120, and assigns to the patient a question group of an adequate education level and symptom level for the patient. At this time, if there are a plurality of question groups in the same level, control section 130 searches for a question group the patient has not answered yet and assigns an unanswered question group to the patient. In this way, by assigning an unanswered question group, it is possible to expect improvement of the patient's education level.

Next, in step S3405, control section 130 asks the medical professional whether the question group assignment for the patient is finished. If the assignment setting is not finished (S3405: "NO"), the process returns to step S3402. On the other hand, if the assignment setting is finished (S3405: "YES"), the process returns to step S3406.

In step S3406, control section 130 makes display section 140 quit displaying the patient assignment screen, and, upon finishing the assigning patient process (step S3400), the process moves to step S3100 of FIG. 6E.

Next, the question answering process (step S4300), answer evaluation process (step S4400) and measurement value evaluation process (step S4600) performed in the patient input/output process (step S4000) of FIG. 6C, will be explained.

Question Answering Process

Figure 9:
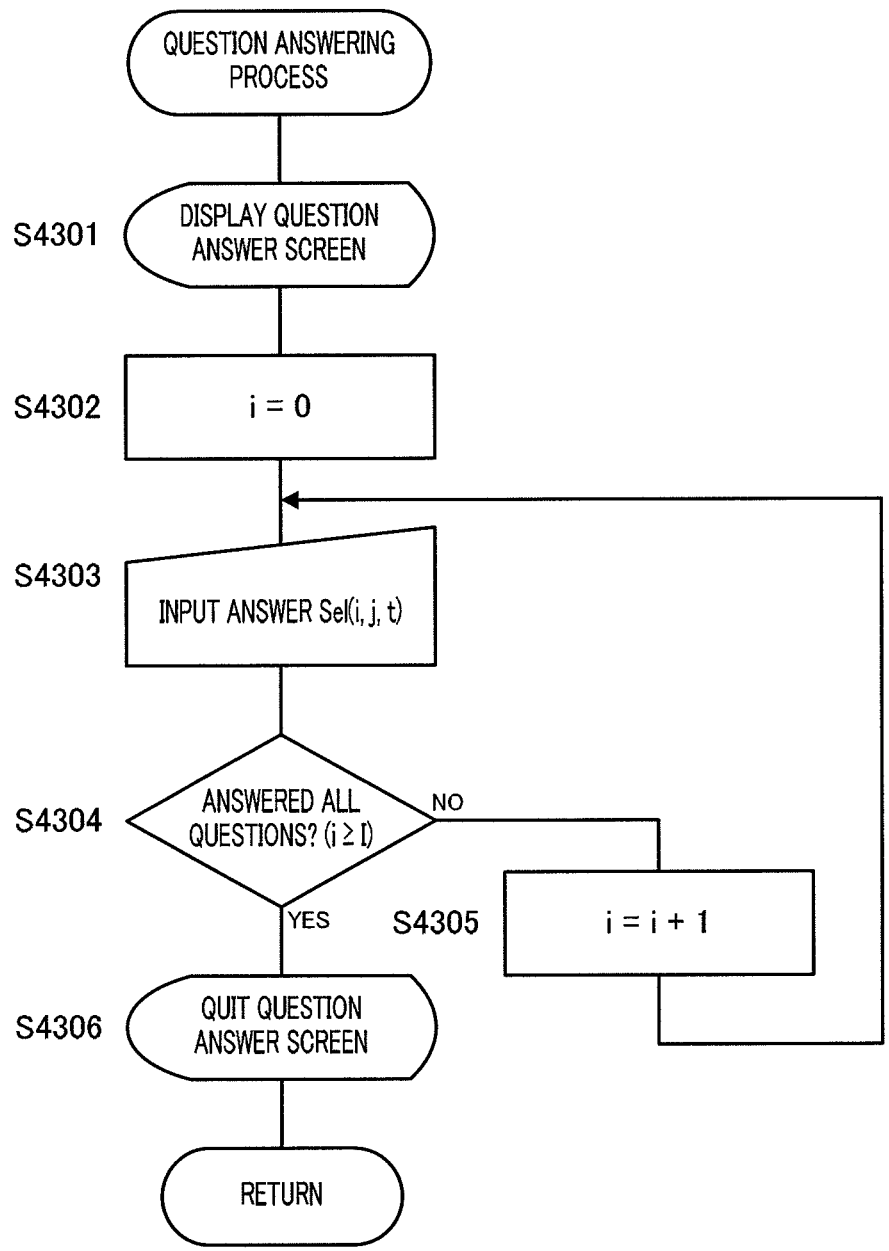
FIG. 9 is a flow chart showing the procedures of the question answering process of FIG. 6C.

First, the question answering process (step S4300) of FIG. 6C will be explained using the flow chart shown in FIG. 9.

First, in step S4301, control section 130 makes display section 140 display the question answer screen and display the questions (question Q(i)) in the question group assigned to the patient (user). Next, in step S4302, control section 130 initializes the questions the patient answers by setting up "i=0".

Next, in step S4303, control section 130 makes the patient input answer Sel(i, j, t) to question Q(i) via input section 110. Here, Sel(i, j, t) represents that the patient chooses the j-th answer option to question Q(i) at time t. Time t is included in the parameters of Sel(i, j, t), because the patient's answer may change over time. For example, even if the patient chooses the right answer by chance without understanding the contents of the question, the patient may not choose the right answer at other times. To eliminate such right answers chosen by chance, reference is made to the history of answers during the right answer rate calculation in the answer evaluation process described later.

Next, in step S4304, control section 130 determines whether the patient has answered all of the questions in the question group, that is, whether "i≧I." If the patient has not finished answering (S4304: "NO"), in step S4305, control section 130 sets up "i=i+1," and the process returns to step S4303. That is, steps S4303 to S4305 repeat until the patient finishes answering all of the questions. On the other hand, when the patient finishes answering (S4304: "YES"), the process moves to S4306.

Figure 6C:
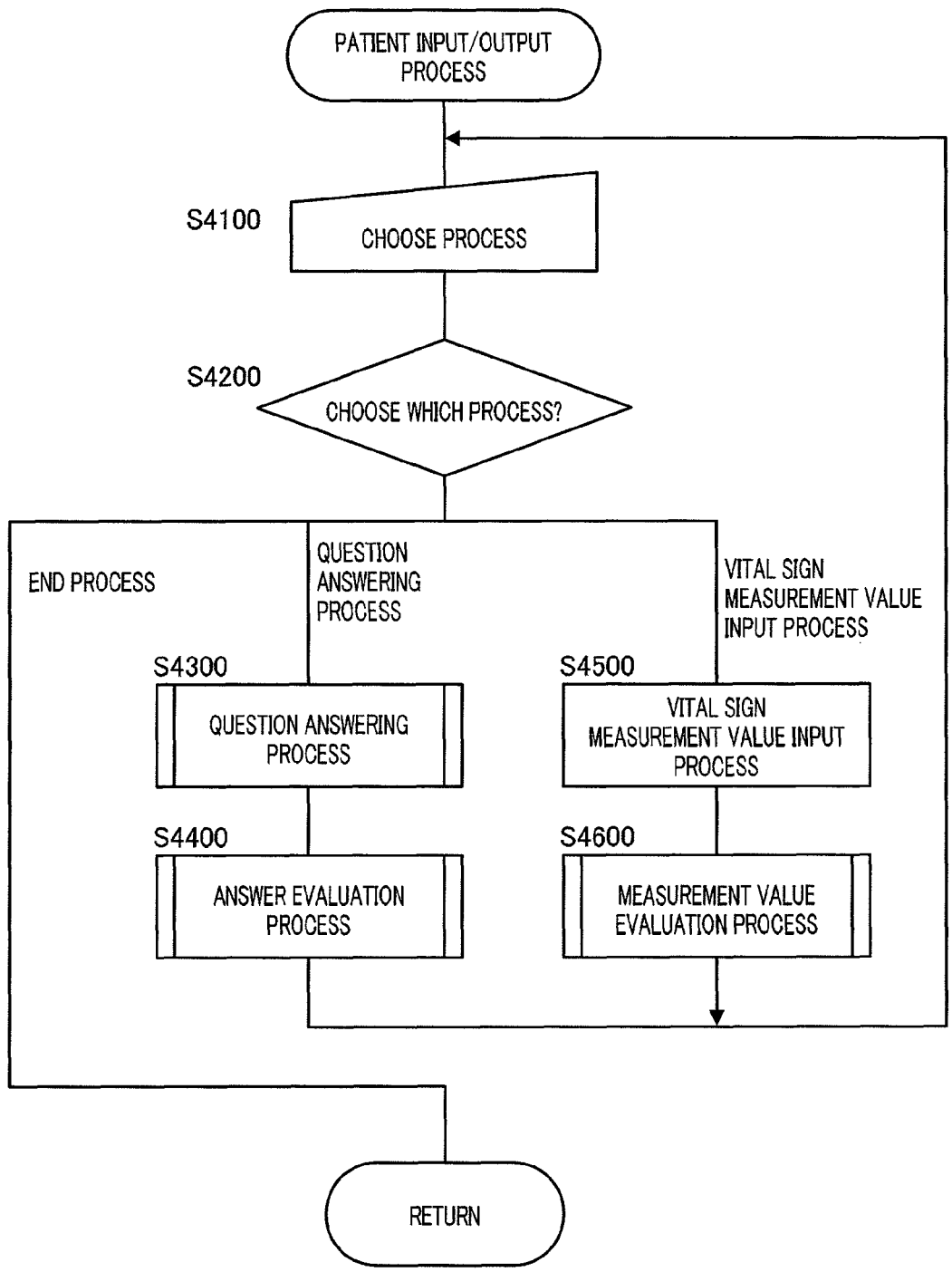
FIG. 6C is a flow chart showing the procedures of the patient input/output process of FIG. 6A.

In step S4306, control section 130 makes display section 140 quit displaying the question answer screen, and, upon finishing the question answering process (step S4300) and the process moves to step S4400 of FIG. 6C.

Answer Evaluation Process

The answer evaluation process (step S4400) of FIG. 6C will be explained using the flow chart shown in FIG. 10A.

First, in step S4401, control section 130 determines whether the patient (user) is the target individual for the automatic assignment function of the question group. If the patient is not the target individual for the automatic assignment function (S4401: "NO"), the control section finishes the answer evaluation process (step S4400) and the process moves to step S4100 of FIG. 6C. On the other hand, if the patient is the target individual for the automatic assignment function (S4401: "YES"), the process moves to S4402.

In step S4402, control section 130 determines whether the right answer rate threshold is set up for the question group assigned to the patient. If the right answer rate threshold is not set up (S4402: "NO"), answer evaluation process (step S4400) is finished and the process moves to step S4100 of FIG. 6C. On the other hand, when the right answer rate threshold is set up (S4402: "YES"), the process moves to step S4403.

In step S4403, control section 130 determines whether the number of times of making references to history for the question group assigned to the patient, is set up.

If the number of times of making reference to history is not set up (S4403: "NO"), in step S4404, control section 130 calculates the right answer rate RAR(n, t) from the answer to question Sel(i, j, t), answer options Ans(i, j) and question weight coefficient W(i), by the algorithm shown in step S4404 of FIG. 10A, and the process moves to step S4406. RAR (Right Answer Rate) includes the question group number n and the time of answer t, as variables.

On the other hand, when the number of times for making reference to history is set up (S4403: "YES"), in step S4405, control section 130 calculates the historical right answer rate HRAR(n) from the answer to question Sel(i, j, t), answer options Ans(i, j), question weight coefficient W(i) and the number of times of making reference to history T, by the algorithm shown in step S4405 of FIG. 10A, and the process moves to step S4406. The HRAR (Historical Right Answer Rate) includes the question group number n as a variable.

In step S4406, control section 130 compares the right answer rate calculated in step S4404 or the historical right answer rate calculated in step S4405 with the right answer rate threshold set up in the question setting process (step S3300) by medical professional, and determines whether the patient's right answer rate (historical right answer rate) is higher than the right answer rate threshold. If the patient's right answer rate (historical right answer rate) is not higher than the right answer rate threshold (S4406: "NO"), control section 130 judges that the patient does not understand well enough the question contents of the question group assigned to the patient, and the answer evaluation process (step S4400) is finished without changing the question group to assign to the patient. On the other hand, if the patient's right answer rate (historical right answer rate) is higher than the right answer rate threshold (S4406: "YES"), control section 130 judges that the patient understands the question contents of the question group assigned to the patient well enough, and the process moves to step S4407. However, if a problem is found in the patient's health conditions from the vital sign measurement values inputted from input section 110, control section 130 may finish the answer evaluation process (step S4400) without changing the question group to assign to the patient, even when the patient's right answer rate (historical right answer rate) is higher than the right answer rate threshold.

In step S4407, control section 130 saves the setup that the patient has finished answering the question group QG(n) in storage section 120. Next, in step S4408, control section 130 searches for a question group the patient has not answered and saves an unanswered question group QG(n+1) to assign to the patient, in storage section 120. By this means the answer evaluation process (step S4400) is finished, and the process moves to step S4100 of FIG. 6C.

Figure 10A:
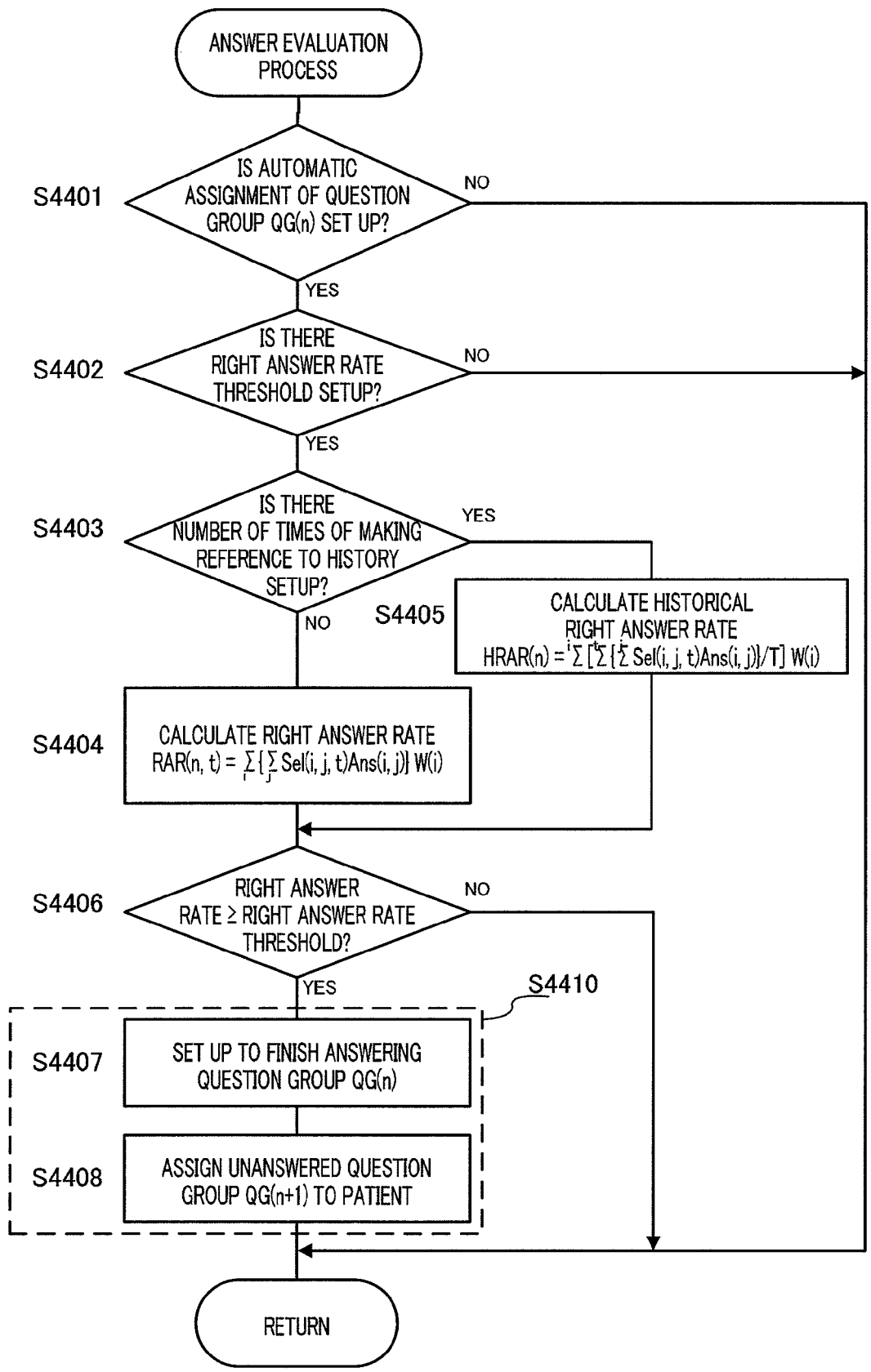
FIG. 10A is a flow chart showing one aspect of the procedures of the answer evaluation process of FIG. 6C.

In the answer evaluation process explained using the flow chart of FIG. 10A, if the patient's right answer rate of the question group is higher than the right answer rate threshold, the question group assigned to the patient is switched to another question group. At this time, the question group to be assigned to the patient is selected from question groups the patient has not answered yet, so that it is possible to expect improvement of the patient's education level.

Figure 10B:
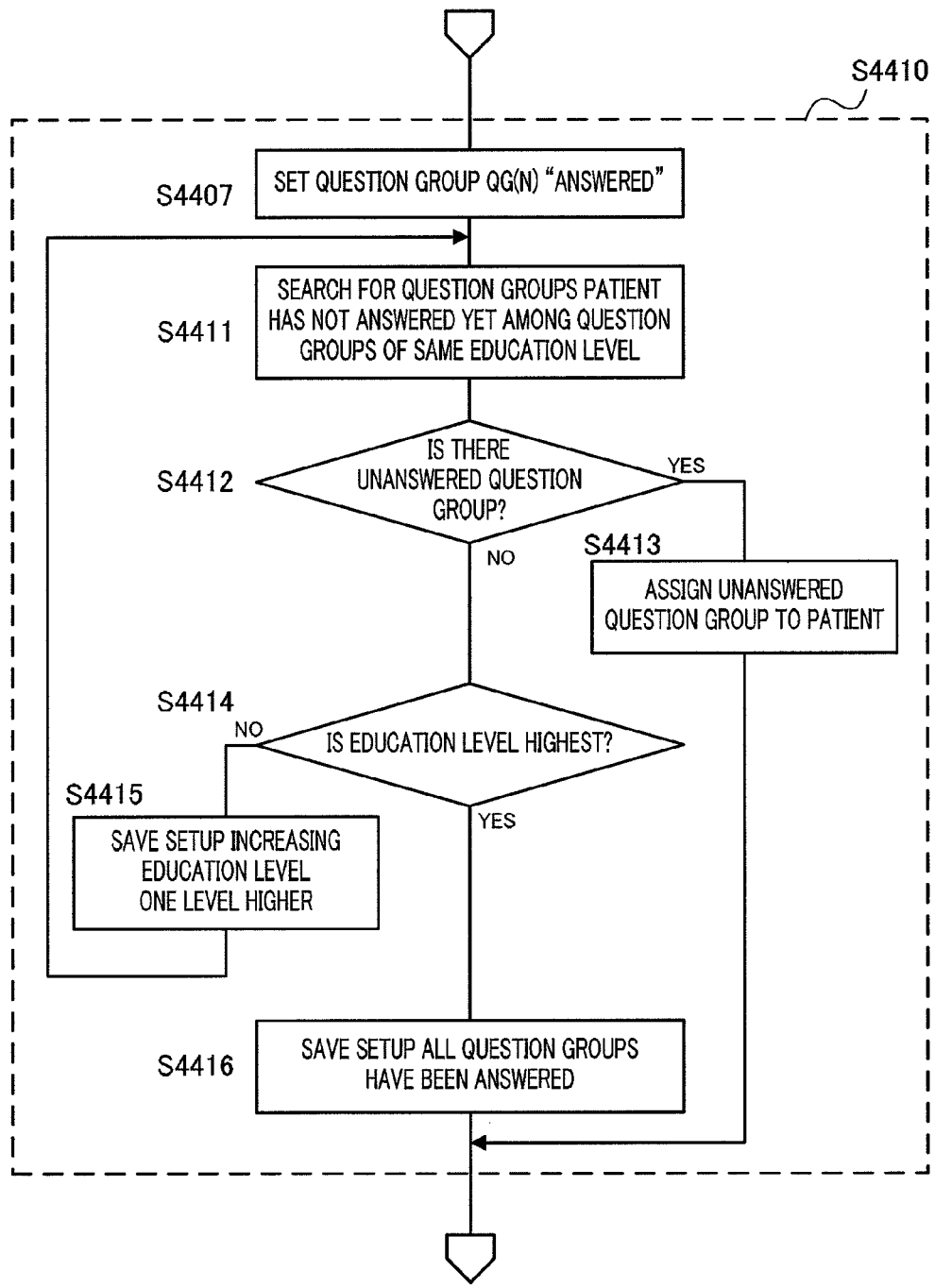
FIG. 10B is a flow chart showing another aspect of the procedures of the answer evaluation process of FIG. 6C.

Here, the answer evaluation process (step S4400) of FIG. 6C will be explained, with reference to a case where the concept of the education level explained in FIG. 5 is introduced into question groups. FIG. 10B shows the process of question group assignment where the concept of the education level is introduced, that is, a flow chart showing the process of step S4410 in FIG. 10A. The answer evaluation process in steps S4401 to S4406 is the same as the process explained in FIG. 10A.

First, when the patient's right answer rate (historical right answer rate) is higher than the right answer rate threshold (S4406: "YES"), in step S4407, control section 130 saves the setting that the patient has finished answering question group QG(n), in storage section 120. Next, in step S4411, control section 130 checks whether in storage section 120 there are question groups the patient has not answered yet among the question groups of the education level presently set with respect to the patient. Next, in step S4412, control section 130 determines whether there are question groups the patient has not answered yet among the question groups of the same education level, in storage section 120. When there are question groups the patient has not answered in storage section 120 (S4412: "YES"), in step S4413, control section 130 saves the setup of assigning the patient an unanswered question group, in storage section 120. By this means, the answer evaluation process (step S4400) is finished, and the process moves to step S4100 of FIG. 6C. On the other hand, if there are not question groups the patient has not answered yet in storage section 120 (S4412: "NO"), in step S4414, control section 130 determines whether the education level set up for the patient is the highest. If the education level is not the highest (S4414: "NO"), control section 130 judges that a higher education level can be set up for the patient than presently set, and the process moves to step S4415. On the other hand, if the education level is the highest (S4414: "YES"), control section 130 judges that a higher education level cannot be set up for the patient than presently set, and the process moves to step S4416.

In step S4415, control section 130 saves the setup increasing the patient's education level one level higher, and the process returns to step S4411.

In step S4416, control section 130 saves the setup that the patient has finished answering all the question groups, in storage section 120. By this means, the answer evaluation process (step S4400) is finished, and the process moves to step S4100 of FIG. 6C.

In this way, in the answer evaluation process introduced the concept of the education level, if the patient's right answer rate for a question group is higher than a predetermined right answer rate threshold, the question group assigned to the patient is switched to a different question group. At this time, if there are question groups the patient has not answered yet in the education level set with respect to the patient, the question group to be assigned to the patient is selected from the unanswered question groups, and, if there are not question groups the patient has not answered yet in the education level set with respect to the patient, the question group to be assigned to the patient is selected from the question groups of one higher education level the patient has not answered yet, so that it is possible to expect improvement of the patient's education level.

Measurement Value Evaluation Process

Figure 11:
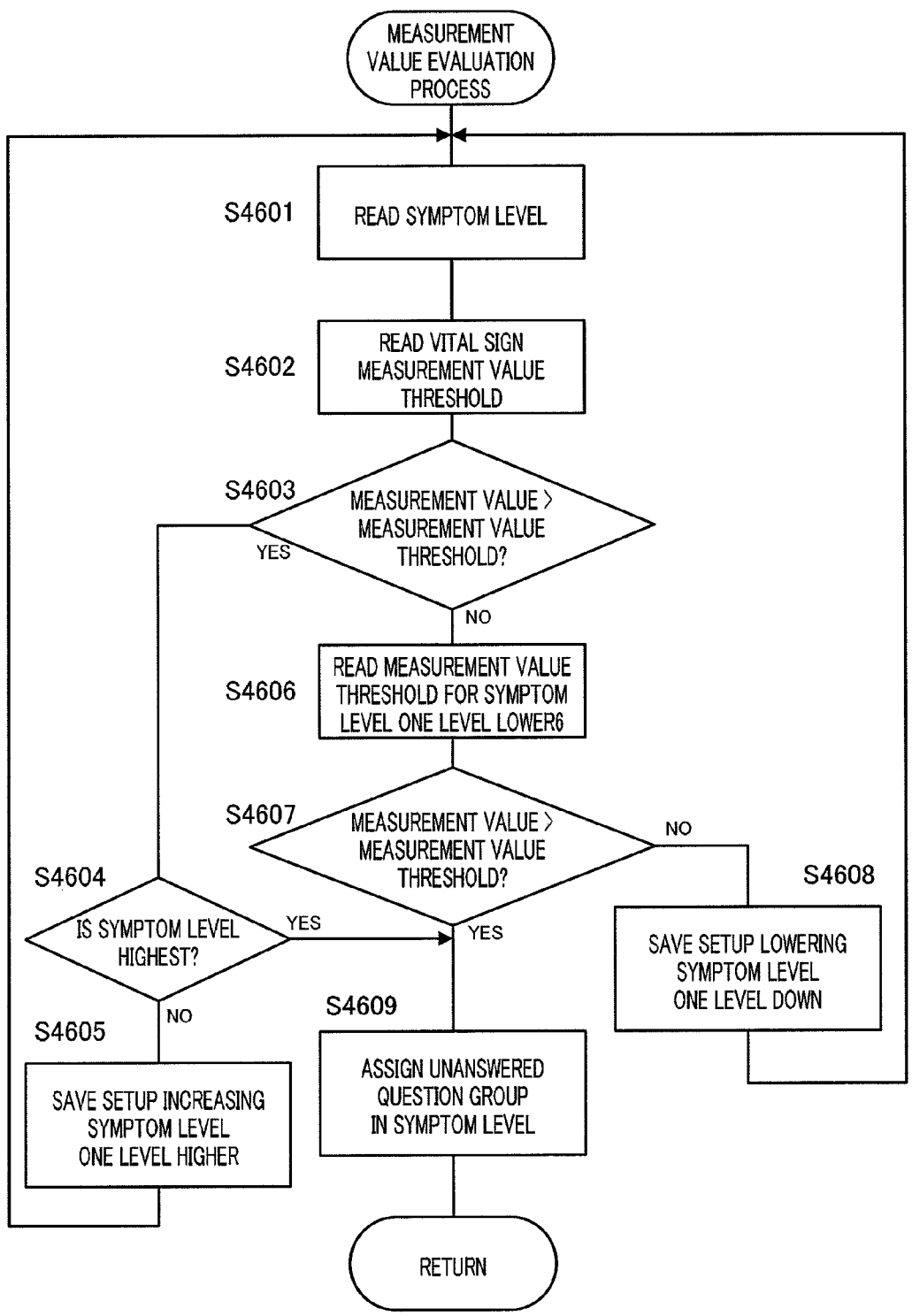
FIG. 11 is a flow chart showing the procedures of the measurement value evaluation process of FIG. 6C.

Lastly, the measurement value evaluation process (step S4600) of FIG. 6C will be explained using the flow chart shown in FIG. 11.

First, in step S4601, control section 130 reads the patient's symptom level set up in advance by medical professional from storage section 120. Next, in step S4602, control section 130 reads the vital sign measurement value threshold of the symptom level set up in advance by medical professional.

Next, in step S4603, control section 130 compares the vital sign measurement value inputted in step S4500 with the vital sign measurement value threshold read in step S4602, and determines whether the vital sign measurement value is higher than the vital sign measurement value threshold. If the vital sign measurement value is higher than the vital sign measurement value threshold (S4603: "YES"), control section 130 judges that the symptom level set up for the patient is inadequately low, and the step moves to S4604.

On the other hand, if the vital sign measurement value is not higher than the vital sign measurement value threshold (S4603: "NO"), control section 130 judges that the symptom level setup for the patient may be inadequately high, and the step moves to S4606.

In step S4604, control section 130 determines whether the symptom level set up for the patient is the highest. If the symptom level is the highest (S4604: "YES"), control section 130 judges that a higher symptom level cannot be set up for the patient than presently set, and the process moves to step S4609. On the other hand, if the symptom level is not the highest (S4604: "NO"), control section 130 judges that a higher symptom level can be set up for the patient than presently set, and the process moves to step S4605.

In step S4605, control section 130 saves the setup increasing the patient's symptom level one level higher, and the process returns to step S4601.

In step S4606, control section 130 reads the vital sign measurement value threshold for the symptom level one level lower than the symptom level presently set.

Next, in step S4607, control section 130 compares the vital sign measurement value inputted in step S4500 with the vital sign measurement value threshold read in step S4606, and determines whether the vital sign measurement value is higher than the vital sign measurement value threshold. If the vital sign measurement value is not higher than the vital sign measurement value threshold (S4607: "NO"), control section 130 judges that the symptom level set up for the patient is inadequately high, and the step moves to S4608. On the other hand, the vital sign measurement value is higher than the vital sign measurement value threshold (S4607: "YES"), control section 130 judges that the symptom level set for the patient is adequate, and the step moves to S4609.

In step S4608, control section 130 saves the setup lowering the patient's symptom level one level down, and the process returns to step S4601.

In step S4609, control section 130 saves the setup assigning the patient an unanswered question group in the symptom level setup for the patient, in storage section 120. By this means, the measurement evaluation process (step S4600) is finished, and the process moves to step S4100 of FIG. 6C.

In this way, in the measurement evaluation process, based on the comparison result between the patient's vital sign measurement value and the vital sign measurement value threshold set up in advance, an adequate symptom level for the patient is set up, so that it is possible to assign to the patient a question group matching his/her symptom level.

Although an example has been explained with the description of the above measurement evaluation process where the upper limit value of each symptom level is used as the vital sign measurement value threshold, the lower limit of each symptom level may be used likewise. Further, judging the symptom level needs not be based on vital sign measurement values alone, and other information may be referred to. For example, with the diabetes disease group, whether or not insulin is administered may also be used in the evaluation of the symptom level.

As described above, the automatic question contents selection system according to Embodiment 1 assesses a patient's education level about health by comparing a right answer rate threshold for questions set up by medical professionals in advance and the patient's right answer rate of answers to the questions, assesses the patient's symptom level by comparing a vital sign measurement value threshold medical professional sets up in advance and the patient's vital sign measurement value, and therefore can automatically choose the questions to assign to the patient based on the patient's education level and symptom level.

Embodiment 2

As described above, conventional question systems have a problem that medical professionals cannot objectively know how much a patient knows about lifestyle improvement and that medical professionals therefore cannot provide appropriate knowledge about lifestyle improvement to the patient. Now, with Embodiment 2, an automatic question system for sending reports for commanding assignment of questions appropriate for a patient based on the patient's right answer rate of answers to questions prepared in advance by medical professional such as doctors and nurses and the patient's health conditions, will be described.

The configuration of the automatic question system is as same as the automatic question contents selection system of Embodiment 1. Further, in the processes performed in the automatic question system of the present embodiment, the processes other than step 54410 (see FIG. 10A) in the answer evaluation process are the same as the processes performed in the automatic question contents selection system of Embodiment 1. Now, step S4410 in the answer evaluation process alone will be explained below.

Figure 12:
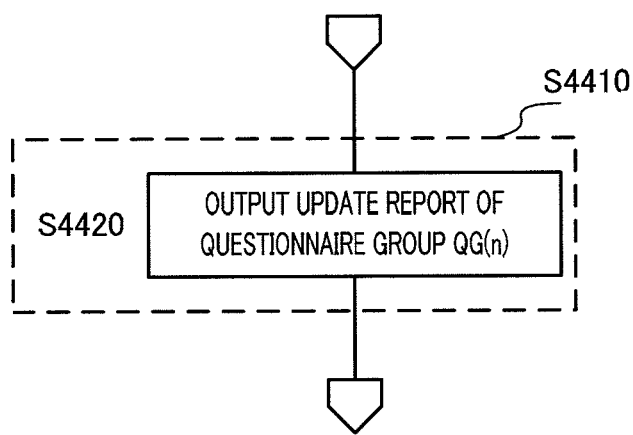
FIG. 12 is a flow chart showing the procedures of the answer evaluation process according to Embodiment 2 of the present invention.

FIG. 12 is the flow chart showing the process of step S4410 in FIG. 10A. The answer evaluation process in steps S4401 to S4406 and the process explained in FIG. 10A are the same.

First, when the patient's right answer rate (historical right answer rate) is higher than the right answer rate threshold (S4406: "YES"), in step S4420, control section 130 notifies medical professional in charge to switch the question group assigned to the patient. As such, the answer evaluation process (step S4400) is finished, and the process moves to step S4100 of FIG. 6C. The method of communicating to medical professionals is not particularly limited; and, for example, there are a method of communicating by sight via monitor displays, a method of communicating by hearing via voice and a method of communicating by touch via vibration. Further, when medical professionals are in remote areas, there are methods of communicating via data communication such as e-mail and methods of communicating via voice such as the telephone, for example.

As described above, the automatic question system of Embodiment 2 can automatically transmit to medical professionals a report to switch the question to assign according to improvement of knowledge of the patient. Consequently, medical professionals can recognize an opportunity for assigning optimal questions for improvement of the patient's lifestyles without missing the opportunity.

Figure 13:
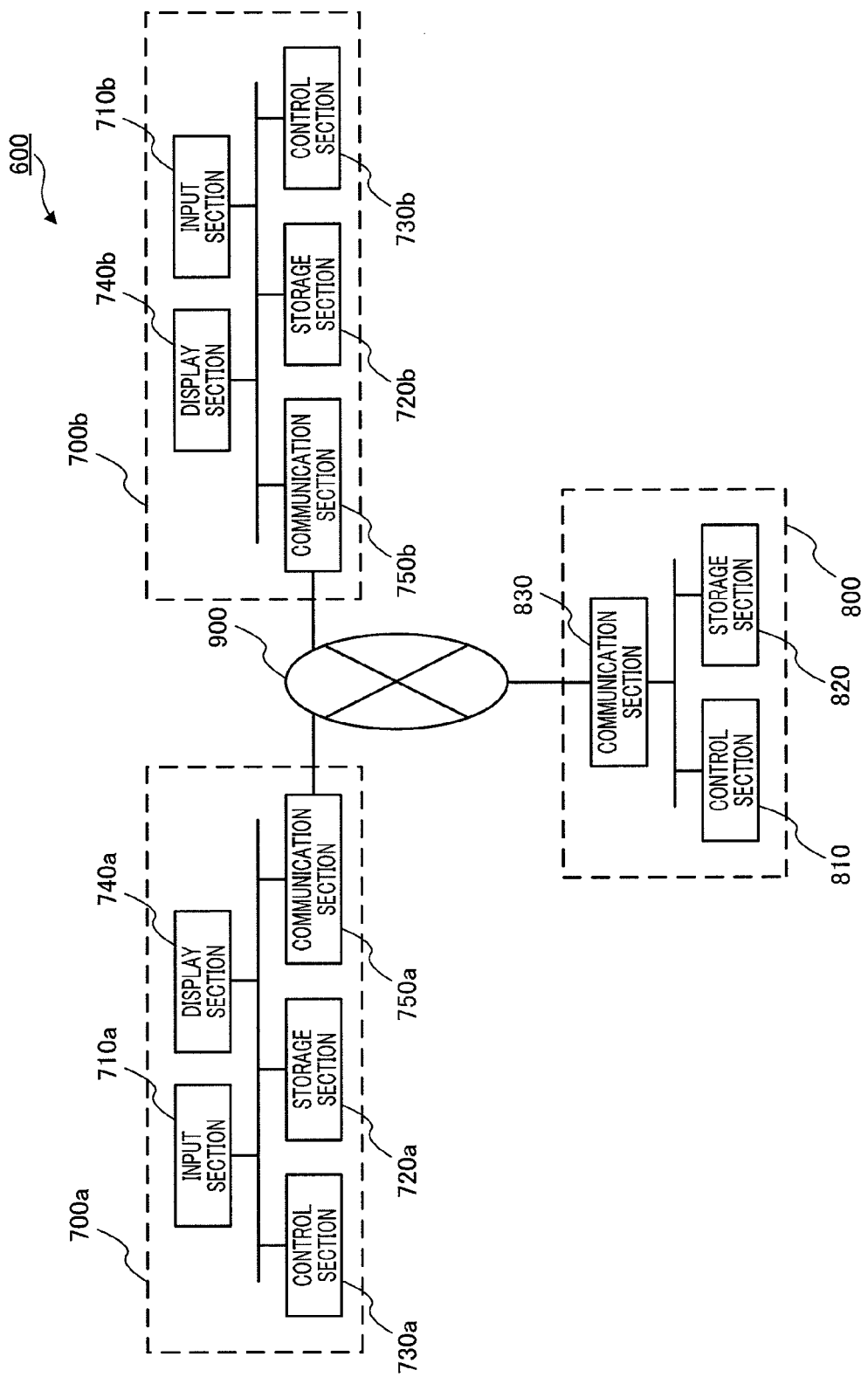
FIG. 13 is a block diagram showing the configuration of the automatic question contents selection system of the present invention comprised of a plurality of apparatuses.

Although cases have been explained with the embodiments presuming medical professionals and the patient use the same apparatus (computer), the automatic question contents selection system of the present invention may be composed of a plurality of apparatuses (computers). For example, the automatic question contents selection system of the present invention may be composed of the terminal for medical professionals, the terminal for the patient and the server as shown in FIG. 13. Hereinafter, the automatic question contents selection system of the present invention composed of a plurality of apparatuses will be explained using the block diagram of FIG. 13.

In FIG. 13, automatic question contents selection system 600 of the present invention is composed of medical professional terminal 700a, patient terminal 700b and server 800, which connect each other via communication line 900. Medical professional terminal 700a has input section 710a, storage section 720a, control section 730a, display section 740a and communication section 750a. Patient terminal 700b has input section 710b, storage section 720b, control section 730b, display section 740b and communication section 750b. Server 800 has control section 810, storage section 820, and communication section 830.

In automatic question contents selection system 600, medical professional operates medical professional terminal 700a to execute medical professional input/output process, and the patient operates patient terminal 700b to execute patient input/output process. At this time, various data and setups prepared by medical professional input/output process or the patient input/output process are stored in storage section 820 of server 800 via communication line 900. Further, the data needed for medical professional input/output process or the patient input/output process is read from storage section 820 of server 800 via communication line 900.

By using this system, patients in areas without medical professionals can easily gain knowledge about health.

The disclosure of Japanese Patent Application No. 2006-143679, filed on May 24, 2006, including the specification, drawings and abstract, is incorporated herein by reference in its entirety.

INDUSTRIAL APPLICABILITY

The present invention makes it possible to assess a patient's education level about health by comparing a right answer rate threshold for questions set up in advance by medical professionals and the patient's a right answer rate to the questions, assess the patient's symptom level by comparing a vital sign measurement value threshold set up in advance by medical professionals and the patient's vital sign measurement value, and automatically choose questions to assign to the patient based on the patient's education level and symptom level. Therefore, the present invention is suitable for use in a system for providing patients with adequate education without requiring medical professionals to keep checking the education levels and symptom levels of patients.

The invention claimed is:

1. A system for automatically selecting question contents, the system comprising:
   an input device that receives as input:
      a question group having at least one question including an inquiry for testing knowledge about health and a plurality of answer options to the inquiry;
      an answer by a respondent to the question of the question group;
      a right answer setting for setting whether or not each of the answer options is a right answer;
      a right answer rate (RAR) threshold for the question group;
      a vital sign measurement value of the respondent; and
      a vital sign measurement value threshold;
   a storage device that stores:
      the question group;
      the right answer setting;
      the RAR threshold;
      the vital sign measurement value threshold; and
   a batch comprising a plurality of question groups, the plurality of question groups being classified into education levels or symptom levels of the respondant and being classified into a matrix having two or more axes, one axis related to the RAR threshold and another axis related to the vital sign measurement value threshold;
   a controller, comprising a processor, that selects a question group from the batch comprising the plurality of question groups to assign to the respondent, based on:
      a RAR comparison result obtained by comparing a RAR of answers by the respondent, calculated from answers input by the respondent through the input and the right answer setting stored in the storage, and the RAR threshold for the question group which the respondent answers; and
      a vital sign measurement value comparison result obtained by comparing the vital sign measurement value of the respondent, received through the input, and the vital sign measurement value threshold stored in the storage; and
   a display that displays:
      the inquiry and the answer options of the question of the question group which the controller assigned to the respondent; and
      the RAR comparison result and the vital sign measurement value comparison result.

2. The system according to claim 1, wherein:
   when the question is a multiple-selection question for choosing at least two answer options in response to one inquiry, in the right answer setting, a plurality of the options for the question may be set up as right answers.

3. The system according to claim 1, wherein:
   the controller reads earlier answers by the same respondent to the question group stored in the storage, and refers to the earlier answers to calculate the RAR for the question group.

4. The system according to claim 1, wherein:
   when the controller calculates the RAR for the question group, the controller assigns a weight to each of the answer options of the question.

5. The system according to claim 1, wherein:
   when the RAR is equal to or higher than the RAR threshold, the controller selects the question group to assign to the respondent from the question groups which the respondent has not yet answered.

6. The system according to claim 1, wherein the plurality of question groups is classified into the education levels, and
   when the RAR is equal to or higher than the RAR threshold, the controller selects the question group, which the respondent has not yet answered, to assign to the respondent from the question groups classified into the same education level.

7. The system according to claim 1, wherein the plurality of question groups is classified into the education levels, and
   when the RAR is equal to or higher than the RAR threshold, the controller selects the question group to assign to the respondent from the question groups of an education level one level higher, in the absence of a question group which the respondent has not yet answered, in the question groups classified into the same education level.

8. The system according to claim 1, wherein the plurality of question groups is classified into the symptom levels, and
   the controller compares the measurement value and the measurement value threshold, and selects the question group from the question groups classified into the symptom level corresponding to the measurement value comparison result.

9. The system according to claim 1, wherein the plurality of question groups are classified into the education levels and the symptom levels.

10. A non-transitory computer readable medium that stores an executable computer program that causes a computer to automatically select question contents, the program causing the computer:
    to receive as input, by performing reception processing of:
       a question group having at least one question including an inquiry for testing knowledge about health and a plurality of answer options to the inquiry;

an answer by a respondent to the question of the question group;

a right answer setting for setting whether or not each of the answer options is a right answer;

a right answer rate (RAR) threshold for the question group;

a vital sign measurement value of the respondents; and a vital sign measurement value threshold;

to perform storage processing of:

the question group;

the right answer setting;

the RAR threshold;

the vital sign measurement value threshold; and a batch comprising a plurality of question groups, the plurality of question groups being classified into education levels or symptom levels of the respondent and being classified into a matrix having two or more axes, one axis related to the RAR threshold and another axis related to the vital sign measurement value threshold;

to perform selection processing by selecting a question group from batch comprising the plurality of question groups to assigned to the respondent, based on:

a RAR comparison result obtained by comparing the RAR of answers by the respondent, calculated from answers input by the respondent and the stored right answer setting stored, and the RAR threshold for the question group which the respondent answers; and a vital sign measurement value comparison result obtained by comparing the vital sign measurement value of the respondent received as input and the stored vital sign measurement value threshold;

to perform display processing to display:

the inquiry and the answer options of the question of the question group which the selection assigned to the respondent; and the RAR comparison result and the vital sign measurement value comparison result.

11. The non-transitory computer readable medium according to claim 10, wherein the plurality of question groups are classified into the education levels and the symptom levels.

* * * * *